United States Patent [19]

Hueil et al.

[11] 4,180,196
[45] Dec. 25, 1979

[54] ANVIL ATTACHMENT FOR A SURGICAL STAPLING INSTRUMENT

[75] Inventors: J. Charles Hueil, Loveland, Ohio;
Robert G. Rothfuss, Bellevue, Ky.;
Terry A. Boothby, Cincinnati, Ohio

[73] Assignee: Senco Products, Inc., Cincinnati, Ohio

[21] Appl. No.: 822,049

[22] Filed: Aug. 5, 1977

[51] Int. Cl.² ............................................. B25C 5/02
[52] U.S. Cl. .................................. 227/109; 227/19; 227/120
[58] Field of Search .................. 227/19, 83, 108, 109, 227/120, 140, 151, 155

[56] References Cited

U.S. PATENT DOCUMENTS

| | | | |
|---|---|---|---|
| 3,873,016 | 3/1975 | Fishbein | 227/83 |
| 4,043,504 | 8/1977 | Hueil et al. | 227/19 X |

*Primary Examiner*—Paul A. Bell
*Attorney, Agent, or Firm*—Melville, Strasser, Foster & Hoffman now Frost & Jacobs

[57] ABSTRACT

An anvil attachment for the nose portion of a surgical stapling instrument of the type utilizing a replaceable cartridge of surgical staples. The anvil attachment is generally "L-shaped". A first leg of the anvil attachment is adapted to lie along and to be affixed to the nose portion of the surgical instrument with the second leg of the anvil attachment extending laterally of the surgical instrument nose portion. Near the juncture of the first and second anvil attachment legs, the second anvil attachment leg is provided on its upper surface with an upstanding wedge-shaped lug which, in cooperation with an adjacent relief on the first anvil attachment leg, engages and maintains the lower end of the staple cartridge in proper position against the nose portion of the surgical stapling instrument. The second anvil attachment leg has a first anvil portion adjacent the wedge-shaped lug and providing a first anvil surface adapted to abut and support the crown of a staple during a staple forming operation. The second anvil attachment leg may have one or more narrower anvil portions adjacent the first anvil portion and providing other anvil surfaces adapted to abut and support the crowns of staples of lesser inside crown dimension during the forming thereof, whereby the anvil may be used with two or more cartridges containing two or more different sizes of staples.

9 Claims, 12 Drawing Figures

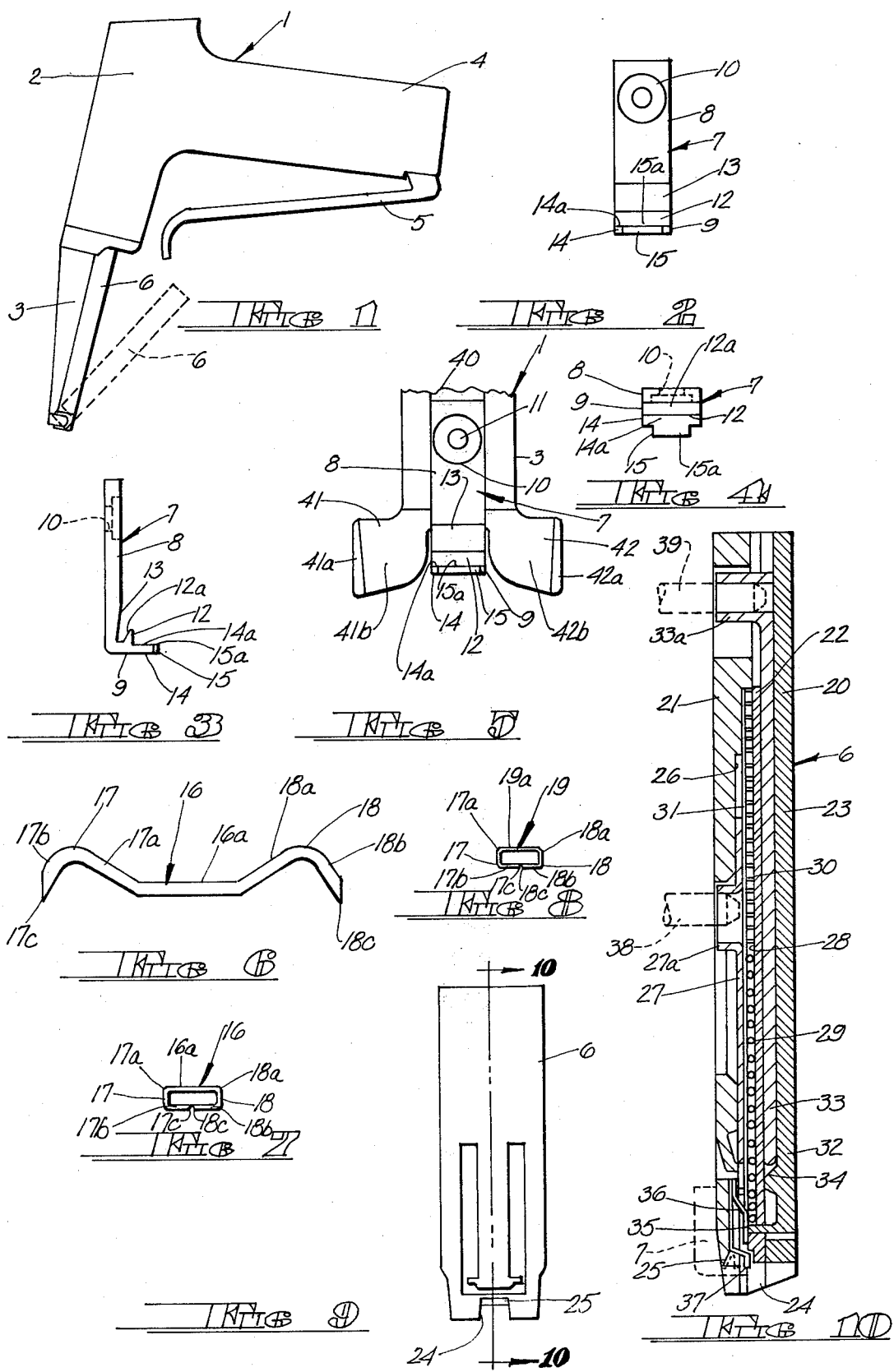

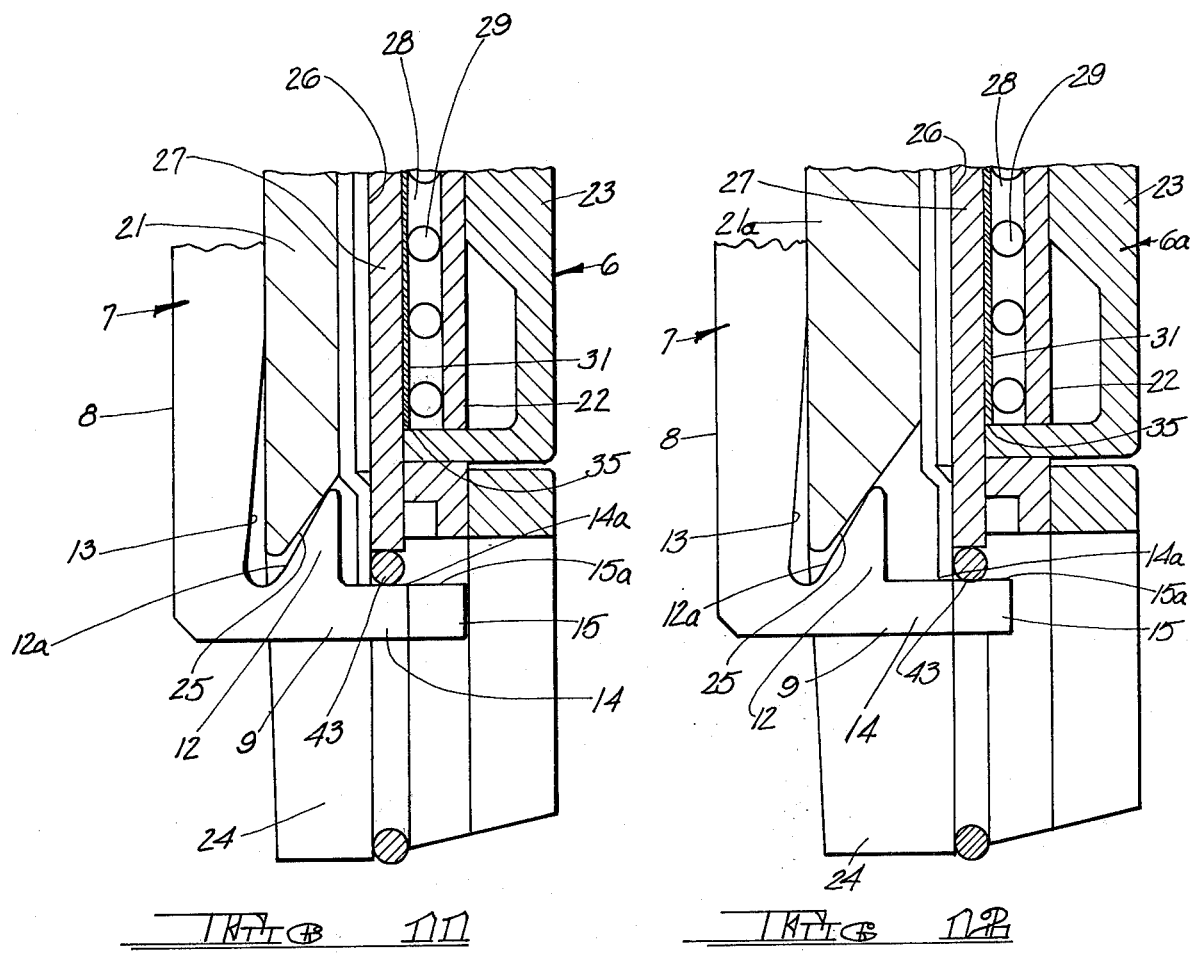

ANVIL ATTACHMENT FOR A SURGICAL STAPLING INSTRUMENT

BACKGROUND OF THE INVENTION

1. Field of the Invention

The invention relates to an anvil attachment about which a staple may be formed during a stapling operation, and more particularly to an anvil attachment to be affixed to the nose portion of a surgical stapling instrument or the like and which may be so configured as to provide anvil portions for two or more different sizes of staples.

2. Description of the Prior Art

While the anvil attachment of the present invention is capable of many applications, it will, for purposes of an exemplary showing, be described with respect to its use on a surgical stapling instrument for which it is particularly well adapted. Recently, surgeons have come more and more to the use of staples, rather than conventional thread sutures, for closing wounds or incisions in the skin and facia of a patient. This trend is due largely to the fact that the use of staples is a far easier procedure and, of even greater importance, is very much faster. This substantially reduces the time required for suturing and the length of time the patient must be maintained under anesthesia.

Prior art workers have devised a number of different types of surgical stapling instruments and staple carrying cartridges therefor. It is the usual practice to provide an anvil (about which the staples are formed) as an integral part of the staple cartridge. Examples of this are taught in the following U.S. Pat. Nos. 3,618,842; 3,638,847; 3,643,851; 3,650,453; 3,662,939; 3,717,294; 3,819,100 and 3,837,555. The provision of an anvil as an integral part of a cartridge structure makes the cartridge structure more complex in design and more expensive to manufacture. In many of the prior art cartridge-surgical stapling instrument systems the cartridge is supported only at one end by the surgical stapling instrument.

The anvil attachment of the present invention is intended to be affixed to the nose portion of a surgical stapling instrument and need not be disposed of with each staple cartridge used. The anvil attachment is intended for use with a cartridge of the type not having an anvil as an integral part of the cartridge. While not necessarily so limited, the anvil attachment is particularly adapted for use with the staple cartridge taught in U.S. Pat. No. 4,043,504.

The anvil attachment provides a simple and positive means for properly locating the staple cartridge on the surgical stapling instrument and for holding the bottom of the staple cartridge accurately and securely to the instrument. The anvil attachment may be configured to accommodate two or more different staple crown widths or sizes and enables simple self-centering of staples of both sizes. The anvil assembly may be readily and quickly attached to and removed from the surgical stapling instrument should replacement of the anvil attachment be necessary or should it be desired to change anvil attachments to accommodate other predetermined sets of staple crown widths.

SUMMARY OF THE INVENTION

The present invention relates to an anvil attachment for the nose portion of a surgical stapling instrument, the stapling instrument being of the type utilizing a replaceable cartridge of surgical staples. The anvil attachment is generally "L"-shaped, having a first leg adapted to lie along and to be affixed to the nose portion of the surgical instrument and a second leg extending laterally of the surgical instrument nose portion.

Near the juncture of the first and second anvil attachment legs, the first leg is provided with a downwardly and inwardly extending relief, while the second leg is provided on its upper surface with an upstanding wedge-shaped lug. The relief in the first leg, the wedge-shaped lug on the second leg and the width of the second leg cooperate to properly locate, center and maintain the lower end of the staple cartridge against the nose portion of the surgical stapling instrument. The surgical stapling instrument, itself, will be provided with means to engage and hold the upper end of the staple cartridge.

The second anvil attachment leg has a first anvil portion adjacent the wedge-shaped lug. This first anvil portion provides a first anvil surface adapted to abut and support the crown of a first size staple during a staple forming operation when a cartridge of such staples is mounted on the nose of the surgical stapling instrument. The upper surface of the second anvil attachment leg may also have a second narrower anvil portion adjacent the first anvil portion. The second anvil portion provides a second anvil surface adapted to abut and support the crown of a second size staple of lesser inside crown dimension during the formation thereof, when a cartridge of such smaller staples is mounted on the surgical instrument nose. Similarly, the second anvil attachment leg may be provided with one or more other anvil portions having anvil surfaces adapted to abut and support the crowns of different sized staples during the formation thereof. Thus, the anvil attachment of the present invention may be designed to accommodate two or more different staple cartridges containing different size staples.

BRIEF DESCRIPTION OF THE DRAWING

FIG. 1 is a semi-diagrammatic side elevational view of a surgical stapling instrument with a staple cartridge mounted thereon and showing in broken lines the initial position of the cartridge during the cartridge mounting procedure.

FIG. 2 is a front elevational view of the anvil attachment of the present invention.

FIG. 3 is a side elevational view of the anvil attachment of FIG. 2 as seen from the left in FIG. 2.

FIG. 4 is a plan view of the anvil attachment.

FIG. 5 is a fragmentary elevational view illustrating the anvil attachment of FIGS. 2-4 mounted on the nose of the surgical stapling instrument of FIG. 1.

FIG. 6 is a front elevational view of an exemplary staple which may be used with the anvil attachment of the present invention.

FIG. 7 illustrates the staple of FIG. 6 in fully formed condition.

FIG. 8 illustrates a staple differing from that of FIG. 7 in that it has a smaller crown dimension.

FIG. 9 is an elevational view of an exemplary staple cartridge of the type to be used with the anvil attachment of the present invention.

FIG. 10 is a cross-sectional view of the staple cartridge of FIG. 9 taken along section line 10—10 of FIG. 9.

FIG. 11 is a fragmentary side elevational view, partly in cross section, illustrating the engagement of the anvil assembly of the present invention with a staple cartridge of the type shown in FIGS. 9 and 10 containing staples of the type shown in FIGS. 6 and 7.

FIG. 12 is a fragmentary elevational view similar to FIG. 11, partly in cross-section, and illustrating the engagement of the anvil attachment of the present invention with a staple cartridge similar to that of FIGS. 9 and 10 containing smaller crown width staples of the type illustrated in FIG. 8.

DESCRIPTION OF THE PREFERRED EMBODIMENTS

An exemplary surgical stapling instrument is illustrated in FIG. 1 and is generally indicated by index numeral 1. The instrument comprises a body 2 having a nose portion 3, a handle portion 4 and an actuator or trigger 5. An exemplary staple-containing cartridge 6 is shown mounted on the nose portion 3 of the instrument. The precise configuration of the surgical stapling instrument and the operating instrumentalities of the surgical stapling instrument do not constitute limitations of the present invention. The instrument may be fluid powered, mechanically actuated by the trigger 5, or the like. The anvil attachment of the present invention (not shown in FIG. 1) is mounted at the free end of nose portion 3, as is illustrated in FIG. 5 and as will be described hereinafter.

The anvil attachment of the present invention is most clearly shown in FIGS. 2 through 4 and is generally indicated at 7. The anvil attachment 7 is made of non-corrosive metal or other appropriate material suitable for use in the operating room environment and capable of withstanding appropriate and well known sterilization techniques. The anvil attachment 7 is generally L-shaped (see FIG. 3) having a first leg 8 with a second leg 9 oriented substantially at a right angle thereto. The leg 8 is provided with a stepped perforation 10 adapted to accommodate the shank and head of a rivet 11 (see FIG. 5) by which the anvil may be affixed to the nose portion 3 of the surgically stapling instrument 1. The head of rivet 11 is preferably flush with the adjacent surface of the anvil attachment 7 to permit a portion of cartridge 6 to lie adjacent thereto, as will be explained hereinafter.

The second leg 9 bears on its upper surface (as viewed in FIG. 3) a wedge-shaped lug 12, providing a lug surface 12a sloping rearwardly and downwardly toward the juncture of legs 8 and 9. The adjacent portion of leg 8 has a downwardly and rearwardly sloping relief 13. The functions of the lug 12 and relief 13 will be described hereinafter.

The second leg 9 of the anvil attachment 7 has a first anvil portion 14. The first anvil portion 14 is of the same width as the leg portion bearing lug 12 and its upper surface constitutes a first anvil surface 14a adapted to abut and support the crown of a staple during a staple forming operation. To this end, the width of the first anvil portion 14 and the first anvil surface 14a is substantially the same as the inside crown dimension of the fully formed staple.

While the leg 9 may terminate at the first anvil portion 14 when the anvil attachment 7 is intended to be used with only one size of staple, it is also within the scope of the present invention to provide leg 9 with one or more other anvil portions if the anvil attachment 7 is to be used with two or more sizes of staples. The present invention is described hereinafter for use with two sizes of staples, and, as can be seen in FIGS. 2, 3, 4, 11 and 12, leg 9 is provided with a second anvil portion 15. The second anvil portion 15 provides at its upper surface a second anvil surface 15a. The second anvil portion 15 and second anvil surface 15a will be of lesser width than the first anvil portion 14 and the first anvil surface 14a, being of a size substantially equal to the inside crown dimension of a fully formed staple having a lesser inside crown dimension than a fully formed staple formed about the first anvil surface 14a.

The anvil attachment 7 of the present invention may be used with any appropriate staple and, as indicated above, is particularly adapted for use with surgical staples, well known in the art. While not intended to constitute a limitation on the present invention, for purposes of an exemplary showing, FIG. 6 illustrates a surgical staple with which the anvil attachment of the present invention may be used and which is taught in U.S. Pat. No. 4,014,492. The staple 16 of FIG. 6 comprises a crown portion 16a terminating in legs 17 and 18. Legs 17 and 18 have first upwardly and outwardly sloping portions 17a and 18a terminating in second, downwardly and outwardly sloping portions 17b and 18b. The staple points 17c and 18c are formed by diagonal cuts across the leg ends. As explained in the above identified U.S. Pat. No. 4,014,492, the cuts forming points 17c and 18c are so arranged as to be perpendicular to the anvil surface 14a of the anvil attachment 7 about which the staple is to be formed and to the skin or fascia of the patient.

FIG. 7 illustrates the staple of FIG. 6 in its fully formed condition and like parts have been given like index numerals.

FIG. 8 illustrates a staple, generally indicated at 19, which is substantially identical to the staple of FIG. 7, differing only in size, its crown 19a having a smaller inside crown dimension. Since the staple 19 of FIG. 8 is otherwise similar to the staple of FIG. 7, again like parts have been given like index numerals. It will be understood that the staple 16 illustrated in FIGS. 6 and 7 will be formed about the anvil surface 14a of anvil attachment 7, while the smaller staple 19 of FIG. 8 will be formed about the anvil surface 15a of anvil attachment 7.

For a better understanding of the anvil attachment of the present invention, FIGS. 9 and 10 illustrate an exemplary cartridge with which the anvil attachment may be used. While the use of the anvil attachment 7 is not necessarily so limited, for purposes of an exemplary showing the cartridge, generally indicated at 6 in FIGS. 9 and 10, is illustrated as being of the type taught in U.S. Pat. No. 4,043,504.

Briefly, the cartridge 6 has a body 20 made up of three basic parts between which all of the remaining parts are located. These basic parts comprise a staple former housing 21, a staple housing 22 and a horizontal feeder housing 23. All three of these parts are configured at their bottom end to provide a tapered notch 24 (see FIG. 9) adapted to just nicely receive the leg 9 of anvil attachment 7. The anvil attachment 7 is shown in broken lines in FIG. 10. The staple former housing 21 has, at its lower end, a downwardly and rearwardly sloping surface 25 adapted to cooperate with the sloping surface 12a of the anvil attachment lug 12, as will be described hereinafter.

The staple former housing provides a staple forming track 26. A staple former 27 is slidably mounted in the staple former track 26. The staple housing has a staple feeding track 28 formed therein adapted to receive a stack of staples 29 and accommodating a sinuous staple advancing spring 30. The staple forming track and the staple feeding track are separated from each other by a thin divider wall 31.

The horizontal feeder housing 23 has an integral resilient tine portion 32 constituting a horizontal feeder. The horizontal feeder housing also slidably mounts a horizontal feeder actuator 33 which cooperates with a cam surface 34 on the horizontal feeder 32 to shift the horizontal feeder from its normal position as shown in FIG. 10 toward the right as viewed in that figure.

The bottom edge of the divider wall 31 and the adjacent portions of the staple housing 22 are so configured as to provide a horizontal passage or "window" 35 through which the bottom most staple of the stack 29 may pass from the staple feeding track 28 to the staple forming track 26. It will be noted that when the horizontal feeder 32 is in its normal position as shown in FIG. 10 it extends into the staple feeding track 28 and underlies the bottom most staple of stack 29.

Spring means 36 are mounted in the staple former housing 21. The spring means 36 also serve to normally close the window 35 and in addition, cooperate with the horizontal feeder 32 to hold a staple in the staple former track in proper position to be engaged by staple former 27. A second spring means 37 is mounted in the staple former housing and assists in disengaging a formed staple from the anvil 7. It will be noted that staple former 27 has a driving eyelet 27a extending through an appropriately configured opening in the staple former housing and adapted to be engaged by a drive pin means 38 of the surgical stapling instrument 1. In similar fashion, the horizontal feeder actuator 33 is provided with a driving eyelet 33a extending through appropriate openings in the staple housing 22 and staple former housing 21 and adapted to be engaged by a drive pin means 39 of the surgical stapling instrument.

In operation, the surgical stapling instrument driving pin means 39 first actuates the horizontal feeder actuator 33 to cause the horizontal feeder 32 to shift out of staple feeding track 28. This permits the lowermost staple of stack 29 to drop under the influence of sinuous spring 30 to a position adjacent window 35. Thereafter, the horizontal feeder actuator 33 is returned by the surgical stapling instrument drive pin means 39 to the position shown in FIG. 10. This permits the horizontal feeder 32 to return to its normal position as shown in FIG. 10 resulting in the fact that the lowermost staple of stack 29 is shoved through window 35 and is held in the staple forming track 26 between the end of the horizontal feeder 32 and the spring means 36. In the mean time, the surgical stapling instrument drive pin means 38 has caused the staple former 27 to begin a downward movement. This downward movement continues until the staple former causes the staple to be formed about the appropriate one of the anvil surfaces 14a or 15a of the anvil attachment 7. The surgical stapling instrument drive pin means 38 at this point causes the staple former 27 to return to its normal position as illustrated in FIG. 10 thereby ending the cycle. Spring means 37 assists in disengaging the formed staple from the anvil attachment 7.

FIG. 5 illustrates the anvil attachment 7 mounted on the nose portion 3 of the surgical stapling instrument 1. FIG. 5 is a fragmentary illustration of nose portion 3 as viewed from the right in FIG. 1. It will be noted that the nose portion 3 has a centrally located, vertical slot 40 of a width to just nicely receive the anvil attachment 7. The anvil attachment may be affixed to the nose portion permanently by means of rivet 11. Alternatively, the hole 10 may constitute a counter sunk hole and the rivet 11 may be replaced by a flat head machine screw enabling the anvil attachment to be removably affixed to the surgical stapling instrument 1. Under these circumstances the anvil attachment, for example, could be replaced by another similar anvil attachment having anvil surfaces so sized as to accommodate staples having other inside crown dimensions.

When the anvil attachment 7 is mounted on the nose portion 3 of the surgical instrument 1, the exposed surface of leg 8 will be substantially flush with the adjacent surfaces of the nose portion. The nose portion may be provided with lateral extensions or wings 41 and 42 having rearwardly extending flanges 41a and 42a. The wings 41 and 42 and flanges 41a and 42a serve to protect the anvil attachment and permit the surgical stapling instrument 1 to be set down upon its side or set down upon flanges 41a and 42a and handle portion 4 without contact between anvil attachment 7 and the surface upon which the surgical stapling instrument 1 is rested.

At this point, the interaction of the anvil attachment 7 and the cartridge 6 can be described as follows. To mount the cartridge 6 on the nose portion 3 of the surgical instrument 1 the cartridge is brought toward the nose portion with the staple former housing side of the cartridge facing the nose portion. The cartridge is brought to the nose portion with the lower end of the cartridge located just above the leg 9 of the anvil attachment and with the cartridge angled with respect to the nose portion (see broken line illustration of cartridge 6 in FIG. 1) such that the included angle therebetween may be up to about 35°. This is made possible by the undercut 13 on the anvil attachment leg 8 and adjacent rearwardly and downwardly sloping surfaces 41b and 42b of wings 41 and 42. The cartridge 6 is then shifted downwardly along nose portion 3 until the anvil attachment leg 9 is received within the cartridge notch 24 and until the surface 12a of the wedge shaped lug 12 of the anvil attachment engages the sloped surface 25 of the staple former housing portion of cartridge 6.

After engagement between surfaces 12a and 25 is established, the cartridge 6 may then be pivoted therebout toward the surgical stapling instrument nose portion 3 until the exterior surface of the staple former housing portion 21 lies adjacent the nose portion 3. The upper end of the cartridge 6 may be held in place by a spring loaded latch (not shown) on the surgical stapling instrument.

The anvil attachment 7 serves several purposes in the mounting of the cartridge 6 on the nose portion 3 of the surgical instrument 1. First of all, it properly centers the cartridge so that the cartridge staples will be correctly formed about the appropriate one of the anvil surfaces 14a or 15a. The anvil attachment also assures that the drive pin means 38 and 39 of the surgical stapling instrument will properly engage with the driving eyelet 27a of the staple driver 27 and the driving eyelet 33a of the horizontal feeder actuator 33, respectively. Finally, the anvil attachment provides a simple, positive means for holding the bottom end of the cartridge accurately and securely to the surgical stapling instrument nose portion 3.

To remove the cartridge from the surgical stapling instrument, the cartridge may be grasped along its edges by the operator's thumb and index finger and pulled away from the surgical stapling instrument nose portion to disengage the upper end of the cartridge 6 from the spring loaded latch on the surgical stapling instrument 1. The cartridge 6 can then be pivoted about the surface 12a of the anvil attachment lug 12 to the position shown in broken lines in FIG. 1. Upon lifting the cartridge slightly to disengage its surface 25 from the anvil attachment lug surface 12a, the removal procedure is complete.

FIG. 11 illustrates the cartridge 6 and the anvil attachment 7 in their relative positions when the cartridge is mounted in place on the nose portion 3 of the surgical stapling instrument. Again, like parts have been given like index numerals. It is immediately evident from FIG. 11 that the interengagement of the sloping surface 25 of the staple former housing 21 of cartridge 6 and the surface 12a of the lug 12 on the leg 9 firmly holds the bottom portion of cartridge 6 in place and insures that the outside surface of the staple former housing 21 of the cartridge 6 abutts the adjacent surface of anvil attachment leg 8 (and hence the adjacent surfaces of the surgical instrument nose portion 3 not shown). The notch 24 at the bottom end of cartridge 6 straddles that portion of the anvil attachment leg 9 bearing the wedge-shaped lug 12 and anvil surface 14a. This portion of anvil attachment leg 9 and the notch 24 are so sized as to have a snug fit, preventing lateral shifting of the cartridge 6 with respect to the nose portion 3 of the surgical instrument.

For purposes of an exemplary showing, the cartridge 6 is illustrated with the staple former 27 in its lowermost position, having formed a staple 43. The staple 43 has been formed about the anvil surface 14a of the anvil attachment and hence is a staple of the larger inside crown dimension capable of being formed on an anvil attachment 7.

FIG. 12 is substantially identical to FIG. 11, differing only in that the cartridge 6a contains staples of the smaller inside crown dimension capable of being formed on the anvil attachment 7. As a consequence, like parts have been given like index numerals. The cartridge 6a of FIG. 12 differs from the cartridge 6 of FIG. 11 only in that its component parts are sized for the smaller size staple and the staple former housing 21a is thicker than the staple former housing 21 of cartridge 6 (FIG. 11) so that the staple former track 26 is so positioned with respect to the leg 9 of anvil attachment 7 that the staple is formed about anvil surface 15a, rather than anvil surface 14a.

In both of the embodiments of FIGS. 11 and 12 the anvil attachment 7 cooperates in a substantially identical manner with the cartridges 6 and 6a. It is particularly evident from FIGS. 11 and 12 that the relief 13 in the leg 8 of the anvil attachment 7 will permit rotation of the cartridge 6 or the cartridge 6a about the surface 12a of lug 12 during attachment of the cartridge 6 or 6a to the nose portion 3 of the surgical stapling instrument 1 and during removal of the cartridge therefrom.

Modifications may be made in the invention without departing from the spirit of it.

We claim:

1. An anvil attachment for the nose portion of a surgical stapling instrument of the type utilizing a replaceable cartridge of surgical staples, said anvil attachment having a first leg configured to lie along and to be attached to said surgical stapling instrument nose and a second leg extending from said first leg at an angle thereto, said second leg having two or more anvil portions about which said surgical staples are formed, each anvil portion being of a width equal to the inside crown dimension of a fully formed staple, and each of said anvil portions having an upper surface comprising a anvil surface adapted to abut and support the crown of a surgical staple during a staple forming operation.

2. An anvil attachment for a surgical stapling instrument of the type utilizing an elongated replaceable cartridge of surgical staples having a staple discharging end, said anvil attachment having a first leg configured to be attached to said surgical stapling instrument and a second leg extending from said first leg at an angle thereto, said second leg having at least a first anvil portion about which said surgical staples are formed and being of a width equal to the inside crown dimension of a fully formed staple, said first anvil portion having an upper surface comprising a first anvil surface adapted to abut and support the crown of a surgical staple during a staple forming operation, means on said second leg of said anvil attachment to engage said staple discharging end of said surgical staple cartridge to properly center said staple discharging end of said cartridge with respect to said first anvil surface and to hold said staple discharging cartridge end in position with respect to said surgical stapling instrument.

3. The structure claimed in claim 2 wherein said anvil attachment is formed of non-corrosive metal suitable for a surgical environment.

4. The structure claimed in claim 2 wherein said second leg of said anvil attachment terminates in a second anvil portion adjacent said first anvil portion, and about which may be formed surgical staples of a different inside crown dimension as compared to said staples formed about said first anvil portion, said second anvil portion having a different width as compared to said first anvil portion and equal to the inside crown dimension of a fully formed staple having different inside crown dimension, said second anvil portion having an upper surface comprising a second anvil surface adapted to abut and support the crown of a surgical staple having said different inside crown dimension.

5. The structure claimed in claim 4 including an upstanding lug located on and extending transversely of the upper surface of said second leg of said anvil attachment, said lug being located between said first anvil surface and the juncture of said first and second anvil attachment legs, said lug having a surface sloping downwardly toward said juncture of said first and second anvil attachment legs, whereby said second anvil attachment leg, at least at the position of said lug, is just nicely receivable in a notch in said surgical staple cartridge discharge end with portions at least of the lug sloping surface and a corresponding sloping surface at the upper end of said surgical staple cartridge notch being in abutment.

6. The structure claimed in claim 5 wherein said first leg of said anvil attachment adjacent said juncture of said first and second legs is relieved so as to slope downwardly and away from said lug.

7. The sturcture claimed in claim 6 wherein said anvil attachment is formed of non-corrosive metal suitable for a surgical environment.

8. The structure claimed in claim 2 including an upstanding lug located on and extending transversely of the upper surface of said second leg of said anvil attachment, said lug being located between said first anvil surface and the juncture of said first and second anvil attachment legs, said lug having a surface sloping downwardly toward said juncture of said first and second anvil attachment legs, whereby said second anvil attachment leg, at least at the position of said lug, is just nicely receivable in a notch in said surgical staple cartridge discharge end with portions at least of the lug sloping surface and a corresponding sloping surface at the upper end of said surgical staple cartridge notch being in abutment.

9. The structure claimed in claim 8 wherein said first leg of said anvil attachment adjacent said juncture of said first and second legs is relieved so as to slope downwardly and away from said lug.

* * * * *